United States Patent [19]

Puffer et al.

[11] 4,358,202

[45] Nov. 9, 1982

[54] APPARATUS AND METHOD FOR MONITORING THE SURFACE CHARACTER OF CIRCULAR OBJECTS

[75] Inventors: Leroy G. Puffer, Vernon; James P. Waters, Ellington, both of Conn.

[73] Assignee: Essex Group, Inc., Fort Wayne, Ind.

[21] Appl. No.: 172,738

[22] Filed: Jul. 28, 1980

[51] Int. Cl.³ .......................................... G01N 21/84
[52] U.S. Cl. ................................. 356/430; 356/445; 356/237; 250/571
[58] Field of Search ............... 356/237, 238, 241, 429, 356/430, 431, 445, 446, 447, 448; 250/562, 563, 571, 572

[56] References Cited

U.S. PATENT DOCUMENTS 4,283,145  8/1981  Miyazawa .......................... 356/237

FOREIGN PATENT DOCUMENTS 746685  11/1966  Canada ................................. 356/429
418775   5/1974  U.S.S.R. .............................. 356/237
727987   4/1980  U.S.S.R. .............................. 356/237

*Primary Examiner*—R. A. Rosenberger
*Attorney, Agent, or Firm*—Stephen A. Schneeberger

[57] ABSTRACT

Apparatus and method for optically scanning the circumference of a generally circular section of a test object, and especially for monitoring the surface character of cables and the like. An optical system has its apparent axis substantially concentric with the centerline of the path along which the cable moves relative to the scanning optics. A beam of radiation is caused to rotate or orbit about that axis and is then directed into near-normal incidence with the surface of the test object such that it is specularly reflected by the surface. The optical system redirects the reflected beam toward one or more detectors, the intensity of outputs of which provide an indication of the surface character of the object.

In a preferred embodiment, a radiation source beam offset from the actual cable path is rotated by a pair of oscillating mirrors such that it describes a divergent conical shape. Certain optics direct a 180° portion of that rotating beam along one path to intersect with a corresponding 180° segment of the cable and a dividing mirror and similar optics direct the other 180° portion of the beam along another path to intersect with the remaining or complementary 180° segment of the cable. By so dividing the beam paths, a full 360° scan of the cable surface is obtained without the cable "shadowing" any part of the incoming beam. The reflected radiation is "returned" along two respective paths to a respective pair of detectors. Some of the optical elements may be movable relative to others to facilitate coupling and uncoupling the apparatus with the cable.

20 Claims, 5 Drawing Figures

APPARATUS AND METHOD FOR MONITORING THE SURFACE CHARACTER OF CIRCULAR OBJECTS

DESCRIPTION

1. Technical Field

This invention relates to apparatus and method for inspecting or monitoring an object or member, and more specifically relates to an optical system for monitoring the surface characteristics of generally circular objects or members which may be elongated, such as cables and the like.

2. Background Art

As part of the process associated with the manufacture of various generally circular products, especially those which are elongated, it is frequently desirable to inspect or continuously monitor the product at one or more stages in its manufacture to assure conformity to design and manufacturing standards and/or to identify certain departures from those standards. One parameter frequently of concern in the manufacture of elongated circular products such as cable is that of surface character or texture. For instance, high voltage electrical cable conventionally consists of a center conductor surrounded by a semiconductive material in turn surrounded by an insulator. The semiconductor material is applied to the center conductor by an extrusion process. It is important that the outer surface of this semiconductive coating be as smooth as possible, inasmuch as various irregularities, and particularly those abrupt discontinuities known as "pips", in the surface of the semiconductive coating can result in in-service cable failure requiring costly repair or replacement. Therefore, it is desirable during or after manufacture to detect any such irregularities in the cable coating surface anywhere about its periphery and along its length, and take appropriate corrective or preventative measures.

It is generally preferable to monitor the product, i.e. coated cable, on line during its manufacture. For that reason, it is preferable to have a non-contact monitoring process which does not inhibit the speed of the manufacturing process nor require the product surface being monitored to be hard and durable at that time. Electrooptical techniques are especially well suited to such monitoring requirements.

Several systems utilized to monitor the surface character and geometry of elongated products such as electrical wire and cable are made by the Zumbach Electronics Corp. of Elmsford, N.J., those Zumbach systems being designated KW 20/60, ODC 26/60, ODAC 24 and ODAC 80. Many of those systems employ optical principles for determining cable diameter and/or surface characteristics. However, they generally employ one, or possibly several, stationary light sources projected transversely of the axis of the cable, and respective detectors are located on the opposite side of the cable. In effect, a shadow profile of the cable, transversely to the beam of projected light is sensed by the detector to provide a limited indication of cable surface characteristics. It will be appreciated that only relatively limited portions of the periphery of the cable are "seen" with such a system, and inspection of a greater portion of the circumference is possible only by either rotating the cable or providing additional sources of light beams.

Another technique for monitoring the surface character of a product is embodied in the Intec System amde by Intec Corp., 10 Glover Avenue, Norwalk, CT. 06852. That system employs a laser to project a beam across the width of a moving chamber to be inspected, and a sensor positioned on the same side of the member detects light reflected by various irregularities in the member surface. However, that system views only the side of the member facing the laser scanner and sensor, and is best suited for monitoring flat rather than curved surfaces.

DISCLOSURE OF INVENTION

It is a primary object of the present invention to provide a system for the complete and accurate inspection or monitoring of the surface of generally circular products, especially elongated circular products such as cable coatings and the like.

It is a further object of the present invention to provide such a monitoring system which is also relatively simple and inexpensive in construction.

It is a still further object of the present invention to provide such a monitoring system capable of online, real time, non-contact operation.

It is an even further object of the present invention to provide such a monitoring system structured to faciliate its installation and removal from the test member.

It is yet a further object of the present invention to provide a monitoring system which is particularly capable of accurately detecting the existence of discontinuities, such as "pips", on the surface of semiconductive coatings on high voltage electrical cables.

According to the apparatus and method of the present invention, a generally circular test object, especially an elongated circular member such as a coated cable, may be inspected or monitored utilizing a system in which a beam of radiant energy is caused to rotate about a line extending through the center of the circle to be scanned on the member. The rotating beam is then directed into incidence with the circular object to be scanned. Where the test member is elongated and is relatively longitudinally moved along a path, the monitoring system includes an optical system for which the apparent axis is substantially coincident with the centerline of the path of the test member, but for which the actual light paths and optical axes are divided and folded and are offset from the test member path. The optical system includes a source beam of electromagnetic radiation, as for instance provided by a laser, and means for rotating that beam about the apparent optical axis. The rotated beam is then directed toward the apparent otpical axis such that it is incident with and scans substantially the entire 360° periphery of a location on the test member path such that the beam is specularly reflected from the entire 360° periphery of the surface of the test member scanned thereat. The beam reflected from substantially the entire 360° periphery of the test member is detected and electrical signals indicative of the intensity thereof are provided. Those electrical signals are then utilized to provide an indication of the surface character, such as roughness, of the test member.

In a preferred embodiment, the source beam is orbitally rotated by two mirrors, each mounted on respective torsion rods having rotational axis orthogonal to each other and being oscillated at a constant amplitude in phase locked 90° phase relationship with each other. The source beam is incident upon one of those two mirrors at its rotational axis, is reflected to the other and is incident therewith along its rotational axis and is reflected from that second mirror at an angle to the axis thereby established such that the orbitally rotated beam describes a substantially conical surface coaxial with the established optical axis. Then, because the established or actual axis of the orbiting beam does not in fact coincide with the test member path, that beam is divided, by a pattern-dividing mirror, into two separate paths in each of which the beam sweeps or orbits through complementary 180° arc portions of a circle. The divided beams are then directed, via various folding mirrors and relay mirrors, to a respective pair of conical reflector segments positioned concentrically on opposite sides of the test member path. The conical reflector segments direct the divided beams to near-normal incidence with the test member path such that, assuming a smooth surface on the test member, the beam is reflected back toward the respective reflector segments where it is again reflected back through the respective optical elements to a pair of detectors located at respective, optically identical, focal points located, in the preferred embodiment, inside the "cone" defined by the incoming rotation beam. However, if the test member surface contains irregularities, the reflected beam will be scattered and displaced by differing amounts from its normal return path such that less or no radiation is sensed at the detectors.

The optical elements associated with one or both of the divided beam paths may be made movable relatively toward and away from one another to facilitate the lateral insertion and removal of a cable.

The detectors provide electrical signals indicative of the intensity of the reflected radiation and those signals are utilized to provide an indication of the texture of the surface of the test member. Circuitry responsive to the detector signal first removes extraneous responses caused by the optics and then determines the average noise level of the signal. That latter value may then be compared with a reference level to indicate when the surface roughness of the test member has exceeded a permissible level.

BEST MODE FOR CARRYING OUT THE INVENTION

Figure 1:
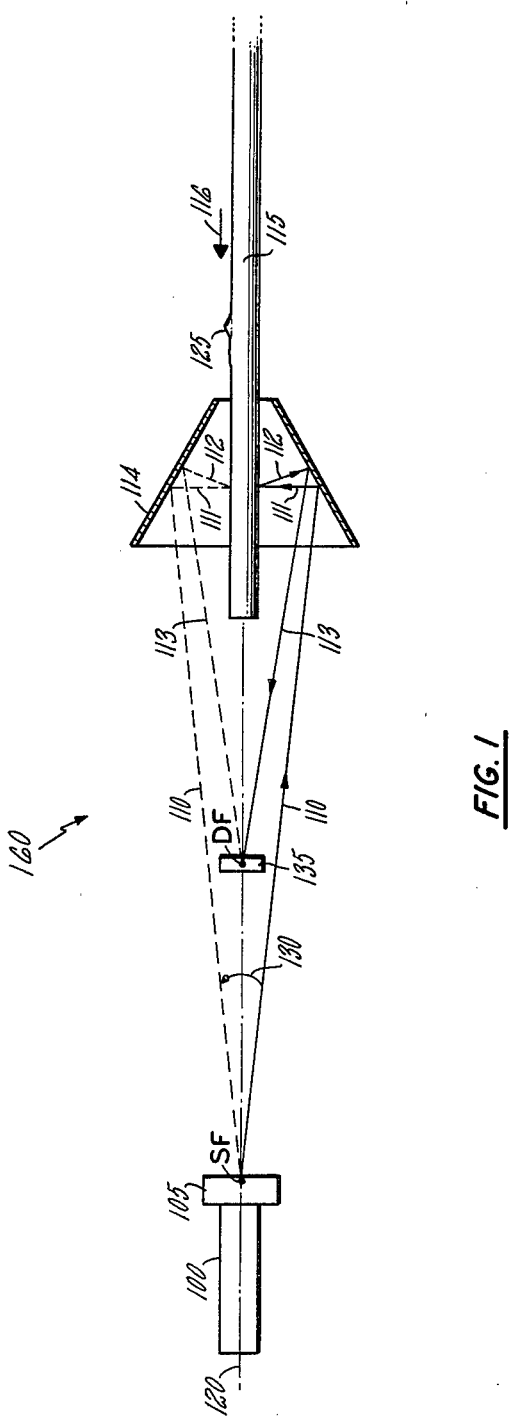
FIG. 1 is a simplified schematic diagram of an idealized equivalent optical system in accordance with the monitor of the present invention.

Referring to FIG. 1, an idealized equivalent optical system 160 for the monitor of the present invention is depicted in simplified schematical diagram form. A generally circular test member, shown here as an elongated coated cable 115, is caused to move along a path 120 in the direction indicated by arrow 116. The cable 115 at this stage of manufacture may range in diameter from less than 0.3 inch to greater than 1.6 inch. In this idealized arrangement, the axis of the optical system to be disclosed also coincides with centerline 120 of the path of the cable 115. In the illustrated embodiment, the cable 115 may typically comprise the metal center conductor and overlying semiconductive coating of a high voltage cable prior to the formation thereover of a tubular insulating covering. The semiconductive coating is generally formed over the center conductor by means of an extrusion process. The outer surface of that semiconductor coating is preferably smooth, however, it may occasionally contain a certain roughness or coarseness of texture which is unesirable, especially if it includes relatively large amplitude irregularities or discontinuities such as "pip" 125. A "pip" is the term given to discontinuities in the cable surface which may be about 1-10 mils more or less in height and 5-40 mils more or less in length or width. The so-called "pips" may give rise to certain voltage breakdown and corona phenomena which can provide damaging to the cable.

In order to detect such pips, preferably prior to the application of the insulating coating, the present optical monitoring system helically scans substantially the entire outer surface of cable 115. More specifically, a relatively thin but intense beam 110 of light, as for instance from a laser 100, at source focus SF on optical axis 120, is caused, by beam rotating mechanism 105, to orbitally rotate about axis 120, as indicated by arrow 130, at an angle to the axis such that its path describes the approximate surface of a cone having its apparent apex at source focus SF and being coaxial with optical axis 120.

The rotating beam 110 is directed toward the inner surface of a truncated conical reflector 114 which is coaxial with the optical axis and cable path 120. The cable 115 moves longitudinally along path 120 through the reflector 114 and generally toward the source focus SF.

The angle of the reflector 114 and the angle therewith of the incident beam 110 are preselected such that the beam is redirected, as beam 11, in a direction which is nearly, but not actually, normal to the cable path 120. Typically, beam 111 will be incident upon cable 115 at an angle of 88° therewith. This slight deviation of incident beam 111 from 90° ensures that the radiant energy reflected from the surface of cable 115 and generally indicated as beam 112 is returned over a path different than that of incident beams 110 and 111 to avoid interference between source and detection elements.

The incident radiant energy of beam 111 is specularly reflected by the surface of cable 115 in a manner providing an indication of the surface character or texture of the cable. More specifically, if the surface of cable 115 were completely smooth, substantially all of the radiant energy would be reflected along beam path 112; however, as the surface texture of the cable becomes rougher or more coarse and/or various irregularities such as pip 125 occur, the reflected energy will be distributed over a larger area and beam 112 will be less well defined.

Finally, the radiant energy of beam 112 is again reflected by conical reflector 114 and is directed as beam 113 toward detector focus DF on the optical axis 120. An optical energy detector 135 positioned at detector focus DF senses the intensity of the radiant energy reflected along the path indicated by beam 113 and provides an electrical signal indicative thereof. It will be appreciated that for a source beam 110 of predetermined intensity, the intensity of the reflected beam 113 precisely at the detector focus DF will be greatest for a perfectly "smooth" surface on cable 115 and will be proportionately less as the texture of the surface of that cable becomes increasingly coarse. Abrupt irregularities of discontinuities, such as pip 125, may deflect so much of the reflected radiation sufficiently away from the illustrated paths 112 and 113 that little or no energy is sensed by detector 135. Accordingly, the electrical signal from the detector 135 is representative of the surface texture of cable 115.

The dotted beam path also designated 110, 111, 112 and 113 is representative of beam 110, 111, 112 and 113 at a moment and position in its orbit which is angularly displaced 180° from the solid line representation thereof.

Recalling that the radiant beam 110 is caused to orbit about the optical axis 120 and that conical reflector 114 is coaxial with axis 120, it will be appreciated that beam 110 is incident with reflector 114 along a circular locus spaced some constant radius from the axis 120. Similarly, the beam 111 will be incident with a circular line about the entire 360° circumference of the surface of cable 115, which circle is substantially coaxial with cable path and optical axis 120 such that the incident beam is uniform about the cable's circumference. Further, the cable 115 is advanced in the direction 116 by known drive means (not shown) such that the actual scan path of the incident beam on the surface of cable 115 is slightly helical. At a cable feed rate of 100 feet per minute or less and a revolving beam scan frequency of about 1 KHz and an effective spot length of 20 mils or more, it is possible to scan substantially the entire surface of the cable.

In actual practice, it is generally not possible to position the radiant energy source 100 and the detector 135 on the cable path 120 inasmuch as cable 115 will necessarily be occupying those locations as it moves therealong. Even if the travel path of cable 115 is caused to bend 90° to that illustrated in FIG. 1 prior to its arrival at detector 135, it will be understood that the cable would then intersect and interrupt or shadow a portion of the conically swept beam 110, thereby preventing a complete circumferential scan of the cable itself. To overcome this situation, the optical system actually developed in accordance with the present invention takes the form generally depicted in FIG. 2.

Figure 2:
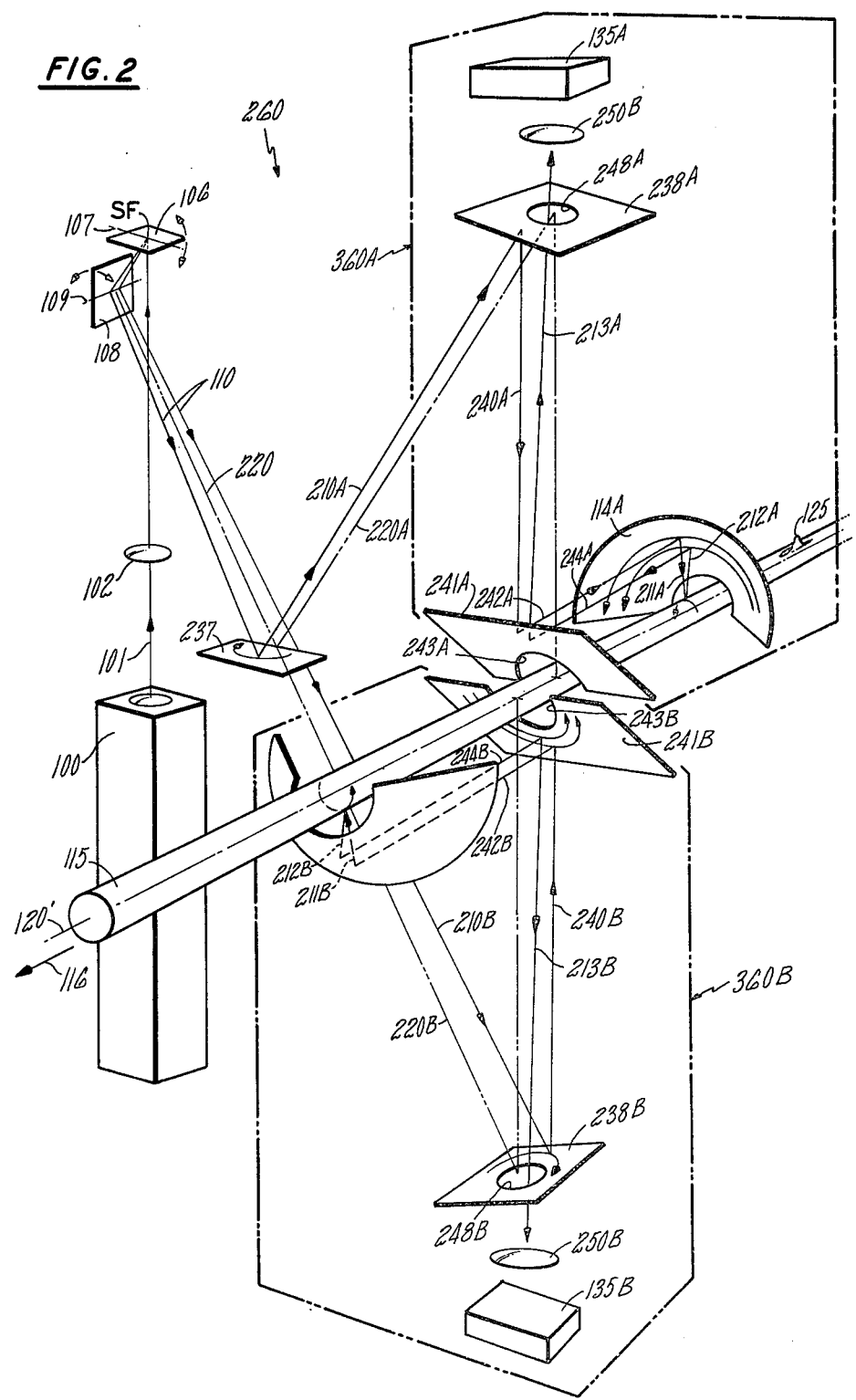
FIG. 2 is a simplified schematic view of an actual optical system in accordance with the monitor of the present invention.

Referring to FIG. 2, the optical system depicted therein is the functional equivalent of that depicted in FIG. 1, but in actuality is somewhat different in structure and orientation. Those elements of FIG. 2 which are identical to those of FIG. 1 are similarly numbered, whereas those elements which are functionally similar but differ in structure or location are numbered such that the "units" and "tens" digits are the same, but the "hundreds" digit is a "two". The remaining reference numerals identify elements not previously considered.

The cable 115 moves in the direction 116 along the path designated by centerline 120'. The centerline 120' of the cable path also corresponds with the equivalent or apparent optical axis of the optical system hereinafter discussed. However, for the reasons previously discussed, the actual axis or axes of the optical system is or are in most instances displaced from the apparent optical axis.

A low-power continuous wave laser 100 provides a beam of electromagnetic radiation 101 directed transversely to the cable path 120' in the illustrated embodiment. The radiation beam 101 is focused by lens 102 to a small "spot" on the surface of cable 115, which spot may have a length of about 30 mils on the cable. The beam 101, after passing through lens 102, is caused to rotate, as beam 110, in a 360° orbit about its optical axis 220 by means of the beam revolving mechanism 105 comprised of oscillating mirrors 106 and 108.

Mirror 106 is disposed transversely to the beam 101 incident therewith and oscillates through a predetermined limited angle about an axis 107. The second mirror 108 is spaced slightly from mirror 106 and oscillates through a predetermined limited angle about axis 109 which extends orthogonally of axis 107. The axes 107 and 109 of the respective mirrors 106 and 108 may comprise respective magnetically driven torsion rods. The relative positions of mirrors 106 and 108 are such that beam 101 is incident upon mirror 106 at a point SF on its axis 107 and is thus reversibly swept by mirror 106 along the line of axis 109 of mirror 108. The torsion rod axis of mirror 108 is controlled to oscillate 90° out of phase with that of mirror 106 such that the beam 110 reflected from mirror 108 is caused to revolve or orbit through 360° about an optical axis 220. This orbiting beam 110 is essentially the same as that of FIG. 1 and describes an approximately conically shaped region having its apex at the source focus SF on mirror 106. In fact, between mirrors 106 and 108, the beam is only moved two-dimensionally, with mirror 108 imparting the three-dimensionality.

Beam 110 is directed in the general direction of cable 115 but at an angle which only brings it near, but not intersecting with, the cable. A fixedly positioned beam dividing mirror 237 intersects 180° of the 360° orbit of beam 110 in a manner such that one-half of the beam is thereby reflected as beam 210A and the other half continues as beam 210B. Each of these "divided" beams, 210A and 210B, describe respective and complementary 180° arcs about their respective axes 220A and 220B, as is illustrated by the arcuate arrows on the various subsequent elements of the optical system. The divergent divided beams 210A and 210B are intersected by respective planar outer or folding mirrors 238A and 238B for redirecting the beams generally toward the cable 115 as arc-traversing beams 240A and 240B, respectively.

A pair of planar relay mirrors 241A and 241B on opposite sides of cable 115 are positioned and oriented so as to redirect respective beams 240A and 240B in opposite directions to one another. These redirected beams, respectively designated 242A and 242B, are incident upon respective conical reflector segments 114A and 114B. Each of the relay mirrors 241A and 241B contains a respective arcuate cut-out or recess 243A and 243B in one side thereof through which cable 115 may substantially coaxially extend such that each mirror "encircles" at least a 180° segment of the cable circumference. The arcuate recesses 243A and 243B are of sufficient radius to pass a range of cable diameters up to 1.5 inches and more.

Each conical reflecting segment 114A, 114B comprises at least about 180°-190° and preferably about 210° of a truncated cone, the axis of which is coincident with the centerline 120' of the cable path. Conical reflector segments 114A and 114B are axially spaced from one another in oppositely facing relationship such that their respective inner surfaces reflect and redirect the beams 242A and 242B toward the cable 115 as beams 211A and 211B, respectively. Beams 211A and 211B are nearly, but not actually, normal to the surface of cable 115 as previously described such that the radiation reflected by the surface of the cable returns along paths 212A and 212B which differ from the respective incident paths 211A and 211B. The radiant energy reflected from the surface of cable 115 and represented by the respective beams 212A and 212B intersects the reflecting surfaces of the respective conical reflectors 114A and 114B along respective arc segments thereof having a different radius from the cable than for the incident beams 211A, 211B. Conical reflectors 114A, 114B then redirect the beams 212A, 212B toward respective relay mirrors 241A, 241B as beams 244A, 244B respectively. The relay mirrors 241A, 241B redirect the respective beams 244A, 244B toward the respective corner mirrors 238A, 238B as beams 213A and 213B respectively.

Each outer mirror 238A and 238B includes a respective aperture 248A and 248B therein through which the respective beams 213A and 213B may pass. The apertures 248A, 248B are concentric with the respective optical axes 220A, 220B of the incident divided beams 210A, 210B and are of sufficiently small area that those beams do not pass through the aperture but are reflected as previously described by those mirrors. However, the returning reflected beams 213A, 213B pass substantially through the center of the apertures 248A, 248B for final focus by respective collecting lenses 250A, 250B on respective detectors 135A and 135B.

Each of the detectors 135A and 135B provides an electrical output signal indicative of the surface texture of the cable 115 along a respective 180° arc line segment of the cable surface, with the combined outputs of the detectors providing an indication of cable surface texture about the full 360° of its circumference.

Figure 3:
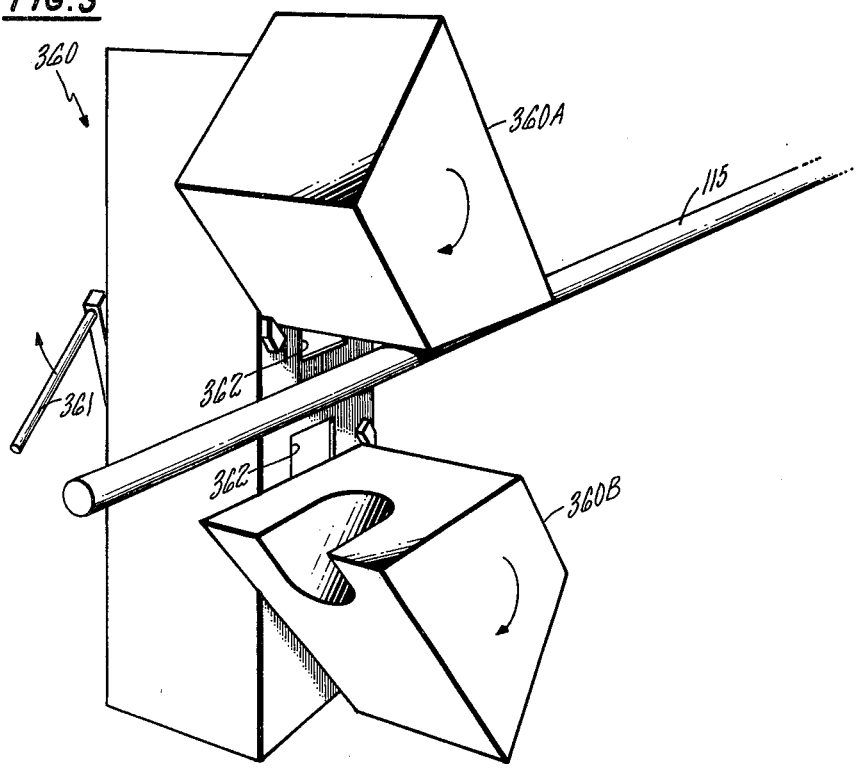
FIG. 3 is a simplified perspective view of one mounting arrangement for the optical system of the monitor of the present invention.

The optical system 260 of FIG. 2 is preferably mounted within an enclosing housing comprised of at least two relatively separable portions to facilitate its installation about cable 115 through relative lateral movement therebetween, rather than requiring end insertion of the cable which could create the need to break the cable from time to time. Referring to FIG. 3, a preferred housing arrangement for the optical system 260 is depicted in which a stationary main housing 360 contains laser 100, beam oscillating mechanism 105 and the beam-dividing mirror 237. Rotatably mounted on one side of housing unit 360 are a pair of relatively separable subhousings 360A and 360B. Subhousing 360A contains those elements of the optical system 260 which are identified by the postscript A in FIG. 2 and are positioned within the dotted line box 360A. Subhousing 360B contains those elements identified by the postscript B and contained within the phantom line box 360B of FIG. 2. Each of the subhousings 360A and 360B is capable of reversible rotation through an angle of about 45° so as to move between the relatively open position, illustrated in FIG. 3, which allows side entry and removal of cable 115, and a relatively closed position (not shown) in which the cable is laterally retained therebetween and the optical elements are positioned as illustrated in FIG. 2. The subhousings 360A and 360B are fixedly mounted on respective rotatable shafts (not shown) which extend through housing 360 and are coupled for joint actuation by means of lever arm 361. Port holes 362A and 362B in the side of housing 360 are in registry with corresponding port holes (not shown) in the respective subhousings 360A and 360B when those subhousings are rotated to the relatively closed position, thereby affording optical communication between the optics of housing 360 and the optics of subhousings 360A and 360B. Each of the housing units is structured to prevent "leakage" of laser light into the environment and, if necessary, an interlocking safety device may be provided to shut off the laser 100 when the subhousings 360A, 360B are moved to the relatively open position.

Figure 4:
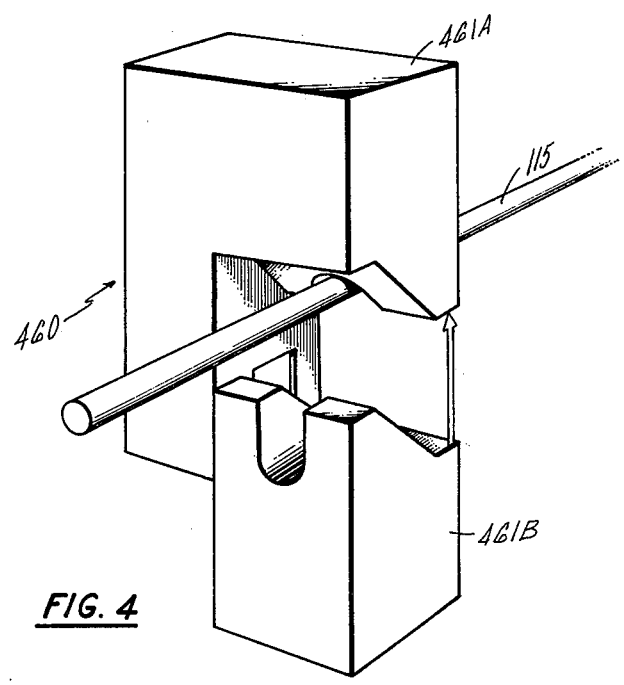
FIG. 4 is a simplified perspective view of an alternate mounting arrangement for the optical system of the monitor of the present invention.

Referring to FIG. 4, there is illustrated an alternate arrangement for housing the optical system 260 of the monitor of the invention. The housing, generally designated 460, is comprised of a first, relatively stationary housing portion 461A and a relatively movable or separable subhousing 461B. The optics common to both the A and B postscripted optical paths, as well as the optics for the A postscripted optical path are contained in the housing portion 461A, and the optics identified by the B postscript in FIG. 2 are contained in the housing subportion B. The housing subportion 461B is slidably joined to housing portion 461A and a suitable linear actuator (not shown) may be manually or automatically actuated to move housing subportion 461B relatively upward from its open position illustrated in FIG. 4 to a relatively closed position in which cable 115 is laterally retained as previously described. Appropriate ports in the respective sides of housing portion 461A and 461B provide the requisite optical communication therebetween.

Figure 5:
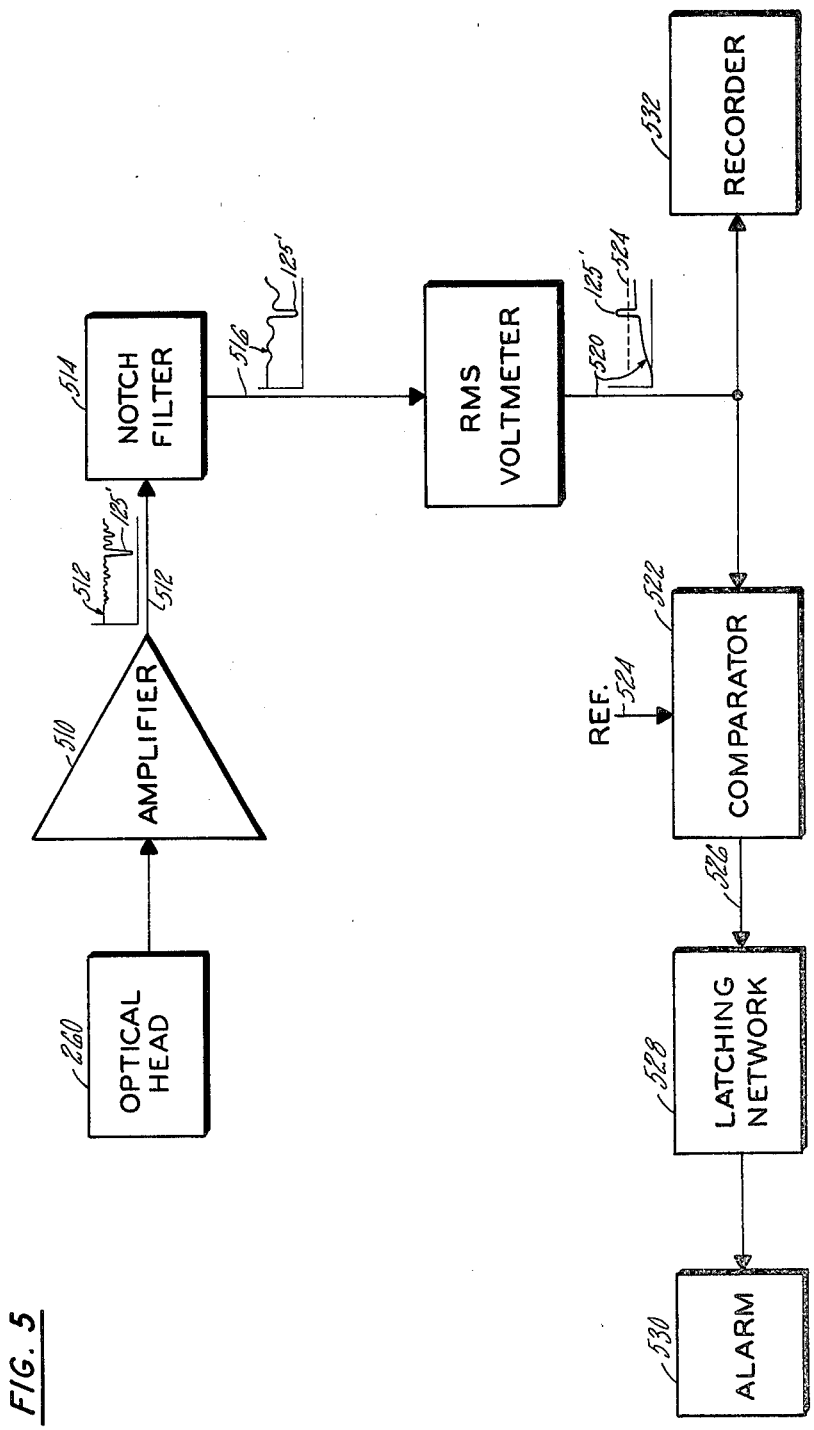
FIG. 5 is a schematic block diagram of the monitor of the invention, including the utilization circuitry.

Reference is now made to FIG. 5 which contains a block diagram illustrating the entire monitor, including the optical system or head 260 and the associated utilization means or circuitry. The output of the optical system 260, and more specifically the electrical signals provided by each detector 135A and 135B are connected in parallel to the input of an amplifier 510 which amplifies the sequential signals and provides a single amplified output signal 512 indicative of the intensity of the sensed radiation reflected from the entire 360° circumference of the cable. It will be appreciated that the signals from the respective detectors 135A and 135B are time-complementary inasmuch as each comprises an opposite 180° segment of the full 360° scan.

The signal 512 is passed through a low pass or preferably a notch filter 514 to reject at least the scanning optical beam frequency, in this instance 1 KHz. This will eliminate extraneous responses from intensity discontinuities caused by the edge of dividing mirror 237 and/or by dirt or other foreign matter which may be on the optics within the head and thus would recur at the scanning frequency. The output 516 of filter 514 should then be representative substantially only of the surface texture of cable 115.

Assuming the surface of cable 115 were completely smooth, the signal 516 would be representative of the maximum possible reflected radiation and would have some particular non-varying DC value. However, the various inconsistencies annd discontinuities which do occur around and along the surface of the cable cause the intensity of the reflected optical signal, and thus electrical signal 516, to vary accordingly, always below the DC value indicative of a smooth surface. The frequency with which these signals vary will be a function of the cable's speed and the immediate topography of the cable surface. Gradual up and down undulations in the surface of cable 115 will be evidenced as relatively low frequency oscillations in signal 516, whereas as abrupt change, such as would be occasioned by pip 125, would result in an abrupt, large-amplitude decrease 125' in the intensity of signal 516. By obtaining the root mean square value of signal 516, as with rms voltmeter 518, a signal 520 is provided which comprises a DC voltage proportional to the average "noise" level of the input signal 516. The signal 520 may then be applied to a comparator 522 for comparison with a reference DC signal 524. Reference signal 524 is of some preselected DC value which is higher than that of signal 520 when the latter is representative of a smooth cable surface, and is selected to evoke an output signal 526 from comparator 522 only when the level of signal 520 exceeds the threshold of maximum permissible roughness. The signal 526 may then be extended to a latching network 528 which maintains the signal for application to alarm circuit 530 which in turn may audibly and/or visually indicate an unacceptable level of surface roughness. Moreover, the output of latching network 528 may provide a control signal which is fed back to the cable extruder for adjusting certain of its parameters in a manner which reduces the roughness of the cable surface. Alternatively, the output 526 of comparator 522 might be connected directly to alarm 530, however, alarming might then occur too frequently and for intervals too brief to be meaningful.

The output 520 of voltmeter 518 may also be extended to a strip chart recorder 532 for providing a hard copy output which will serve as a record of the surface texture of the cable. Such record may be used as proof of the flaw-free character of the surface of the cable or, alternatively, can be used to locate major flaws which could subsequently be cut from the cable.

Although the present invention has been shown and described with respect to preferred embodiments thereof, those skilled in the art should understand that various changes and omissions in the form and detail thereof may be made therein without departing from the spirit or scope of the invention.

For instance, the invention may be utilized to inspect or monitor generally spherical test members, not necessarily elongated nor moving along a linear path. The invention provides the technique and means for performing a uniform circumferential scan of a circular member.

As a further example, assuming a cable or the like is to be monitored and some limited shadowing of the inspection beam may be tolerated, it would be possible to circumferentially scan a large angular portion (i.e. 180°–340°) of the cable using but a single rotating beam having an acceptable portion (i.e. 20°–180°) of the orbit interrupted by the cable. In such instance, a single conical reflector and a single relay mirror, each possibly having a 60°+ slot or recess therein for removable positioning about the cable, may be the only reflective elements required (beyond the beam rotator) to afford a 180°–340° or more arcuate scan of the circular member.

Having thus described a typical embodiment of our invention, that which we claim as new and desire to secure by Letters Patent of the United States is:

1. Apparatus for monitoring the surface character of an elongated generally circular test object, such as a coated cable, the test object being longitudinally movable along a path relative to said apparatus, said apparatus comprising:

an optical system having an apparent axis substantially coincident with the centerline of said test object path, said optical system comprising means for providing a source beam of electromagnetic radiation, means for rotating said beam about the apparent optical axis, means for dividing the rotating source beam into a plurality of beams, each beam of the plurality traversing an arc of predetermined angular extent about its own respective optical axis, at least one of said divided-beam axes differing from said apparent optical axis, the cumulative angle traversed by said plurality of divided beams being at least about 360°, means for directing each of said plurality of divided beams toward said apparent optical axis such that it is incident with and scans a respective arcuate segment of the 360° circumference of any said test object thereat, thereby avoiding interruption of said rotating beam by a test object on said object path and affording a scan of the entire 360° circumference of any said test object such that the beam is reflected by the scanned portion of the circumference of the surface of any said test object thereat, and means for detecting the beam reflected from said scanned portion of the circumference of the test object and providing electrical signals indicative of the intensity thereof; and utilization means responsive to said electrical signals for providing an indication of the surface character of the test object.

2. The apparatus of claim 1 wherein said means for rotating said source beam of radiation comprises source reflecting means mounted for angular displacement such that said source beam orbitally rotates at an angle to said apparent optical axis, said orbitally rotated source beam describing a substantially conical shape having said apparent optical axis as its axis.

3. The apparatus of claim 2 wherein said means for orbitally rotating said source beam of radiation comprises two oscillatory mirrors each having a rotational axis orthogonal to the other and being oscillated about their respective axes 90° out of phase with each other, said source beam of radiation being incident upon a first one of said mirrors substantially on its respective said axis.

4. The apparatus of claim 3 wherein each of said mirrors is mounted on a respective torsion rod, said torsion rod forming the oscillation axis of a respective said mirror, and each said torsion rod being oscillated at a constant amplitude and in phase-locked 90° phase relation with the other.

5. The apparatus of claim 2 wherein the extent of said beam axially of said test member at its said incidence with said test object, in combination with the frequency at which said rotating beam orbits and with the velocity of relative axial motion between said test object and said beam incident therewith, provides an overlapping helical scan along the length of said elongated test object.

6. The apparatus of claim 1 wherein said detecting means comprises optical focusing means and a plurality of detectors, said optical focusing means being operative to focus, at a respective detection focal point on each of the respective divided beam axes, respective different portions of said portion of the beams reflected from the entire circumference of the test object, and each detector of said plurality being positioned substantially at a respective different one of said detection foci.

7. The apparatus of claim 6 wherein said plurality of detectors comprises two detectors.

8. The apparatus of claim 6 wherein said optical focusing means comprises truncated substantially conical reflecting means, the axis of said conical reflecting means being substantially coincident with the apparent optical axis and said object path for reflecting and focusing said portion of the beams reflected by the test object.

9. The apparatus of claim 7 wherein said means for rotating said source beam of radiation comprises source reflecting means having said source beam incident thereon and being mounted for angular displacement such that said source beam orbitally rotates at an angle to its optical axis, to thereby describe an approximately conical shape centered about and having its apex at a source focus on its optical axis.

10. The apparatus of claim 9 wherein said beam directing means also includes said conical reflecting means, said divided beams each being incident upon respective angularly displaced arc segments of said conical reflecting means at a first radius from said apparent optical axis for redirection toward said test object path at an incident angle nearly normal thereto, said incident angle with said test object that being preselected such that said portions of the beam reflected from the surface of a test object are reincident with said conical reflecting means along respective angularly displaced arc segments thereof substantially at a second radius from said apparent optical axis, said second radius being different than said first radius whereby to avoid coincidence of said detection foci with said divided beams prior to their said incidence with a test object.

11. The apparatus of claim 10 wherein said plurality of detectors comprises only two detectors.

12. The apparatus of claim 11 wherein said conical reflecting means comprises two discrete arcuate segments of a truncated conical reflector, each said arc segment being at least about 180° in angular extent and being positioned on respectively opposite sides of the test object path.

13. The apparatus of claim 12 wherein said means for dividing said rotating source beam into said plurality of beams comprises a dividing mirror, said dividing mirror being optically intermediate said source focus and said conical reflecting means and being positioned to intersect and reflect only substantially 180° of said beam orbit.

14. The apparatus of claim 13 wherein said beam directing means and said optical focusing means additionally include a pair of relay mirrors and a pair of outer mirrors, each mirror of said pair of relay mirrors being positioned adjacent to the test object path on respectively opposite sides thereof and optically intermediate said conical reflecting means and both said beam dividing mirror and said detection foci for relaying said respective divided beams directed toward and reflected from a said test member and each outer mirror being optically intermediate said relay mirrors and said beam dividing mirror for folding the respective divided beams.

15. The apparatus of claim 14 wherein said relay mirrors adjacent to said test object path are planar and each includes, as does each of said conical reflector segments, a substantially arcuate recess therein, said arcuate recesses being substantially coaxial with the apparent optical axis and the test object path, and the radii of said arcuate recesses being sufficient to accept a range of test members diameters therebetween.

16. The apparatus of claim 15 wherein said conical reflector segments are axially spaced from each other along the test object path in axially-opposed facing relation such that said respective divided beams directed therefrom and incident upon said test object path are also axially spaced from each other.

17. The apparatus of claim 14 wherein said two conical reflector segments, said pair of relay mirrors, said pair of outer mirrors and said two detectors comprise two separate optical paths, each said optical path being for a respective one of said divided beams, the conical reflector segment, relay mirror, outer mirror and detector comprising one said optical path being movable in unison relative to the conical reflector segment, relay mirror and detector comprising the other said optical path, such that at least said conical reflector segment and relay mirror of said one optical path are movable relatively toward and away from said conical reflector segment and relay mirror of said other optical path to facilitate introduction and removal from therebetween of a test object.

18. The apparatus of claim 1 wherein said beam directing means comprises truncated, substantially conical reflecting means, the axis of said conical reflecting means being substantially coincident with the apparent optical axis and each of said divided rotating beams being incident upon respectively different, angularly displaced arc segments of said conical reflecting means for redirection toward said test object path at an angle nearly normal thereto.

19. The method of optically monitoring the surface character of an elongated generally circular test object, such as a coated cable, the test object being longitudinally movable along a path relative to said apparatus, comprising the steps of:

generating a source beam of electromagnetic radiation;

rotating said beam about an apparent optical axis, said apparent optical axis being coincident with the centerline of the test object path;

dividing the rotating source beam into a plurality of beams, each beam of the plurality traversing an arc of predetermined angular extent about its own respective optical axis, at least one of said divided-beam axes differing from said apparent optical axis, the cumulative angle traversed by said plurality of divided beams being at least about 360°;

directing each of said plurality of divided beams toward said apparent optical axis such that it is incident with and scans a respective arcuate segment of the 360° circumference of any said test object thereat, thereby avoiding interruption of said rotating beam by a test object on said object path and affording a scan of the entire 360° circumference of any said test object such that the beam is reflected by the scanned portion of the circumference of the surface of any said test object thereat;

detecting the beam reflected from said scanned portion of the circumference of the test object and providing electrical signals indicative of the intensity thereof; and indicating from said electrical signals the surface character of the test object.

20. The method of claim 19 wherein said step of rotating said source beam comprises rotating said beam at an angle to said apparent optical axis, said orbitally rotated source beam thereby describing a substantially conical shape having said apparent optical axis as its axis.

* * * * *